(12) United States Patent
Carpenter

(10) Patent No.: US 7,816,147 B2
(45) Date of Patent: Oct. 19, 2010

(54) BIOSENSOR COMPRISING PLANT CELLS CAPABLE OF EXHIBITING A STATE CHANGE MEASURABLE OPTICALLY

(75) Inventor: Steven E. Carpenter, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 762 days.

(21) Appl. No.: 11/593,227

(22) Filed: Nov. 6, 2006

(65) Prior Publication Data

US 2007/0231786 A1 Oct. 4, 2007

Related U.S. Application Data

(62) Division of application No. 10/245,678, filed on Sep. 16, 2002, now Pat. No. 7,141,414.

(51) Int. Cl.
 *G01N 21/76* (2006.01)
 *C12N 5/00* (2006.01)
 *C12M 3/00* (2006.01)

(52) U.S. Cl. .................. 436/172; 435/420; 435/29; 435/287.1; 435/288.7

(58) Field of Classification Search ............... None
See application file for complete search history.

(56) References Cited

U.S. PATENT DOCUMENTS

| 5,441,873 A | 8/1995 | Knight et al. |
|---|---|---|
| 5,580,785 A | 12/1996 | Stiffey et al. |
| 5,631,171 A | 5/1997 | Sandstrom et al. |
| 5,702,915 A | 12/1997 | Miyamoto |
| 5,834,218 A | 11/1998 | Gemillet |
| 5,851,489 A | 12/1998 | Wolf et al. |
| 5,922,550 A | 7/1999 | Everhart et al. |
| 6,060,256 A | 5/2000 | Everhart et al. |
| 6,117,643 A | 9/2000 | Simpson et al. |
| 6,210,910 B1 | 4/2001 | Walt et al. |
| 6,221,579 B1 | 4/2001 | Everhart et al. |
| 6,225,108 B1 | 5/2001 | Larsen et al. |
| 6,277,629 B1 | 8/2001 | Wolf et al. |
| 6,649,417 B2 | 11/2003 | Greenbaum et al. |
| 6,869,763 B1 | 3/2005 | Tamura et al. |
| 2001/0028032 A1 | 10/2001 | Church et al. |

OTHER PUBLICATIONS

Yun et al. Variations of Photosynthetic Activity and Growth of Freshwater Algae According to Ozone Contact Time; Biotechnology Letters, vol. 19, No. 9 (1997 )pp. 831-833.*
Brack et al. Chlorophyll a Fluorescence: A Tool for the Investigation of Toxic Effects in the Photosynthetic Apparatus; Ecotoxicology and Environmental Safety, vol. 40 (1998) pp. 34-41.*
Singh, P.K. Effect of Pesticide on Blue-Green Algae; Arch. Mikrobiol., vol. 89 (1973) pp. 317-320.*
Nothnagel et al. Fluorescence Studies on Modes of Cytochalasin B and Phallotoxin Action on Cytoplasmic Streaming in Chara; The Journal of Cell Biology, vol. 88 (1981) pp. 364-372.*
Koop et al. Chloroplast Migration: A New Circadian Rhythm in Acetabularia; Protoplasma, vol. 97 (1978) pp. 301-310.*

* cited by examiner

*Primary Examiner*—Rebecca E. Prouty
*Assistant Examiner*—Paul C. Martin

(57) ABSTRACT

The illustrated embodiment comprises a biosensor utilizing plant cells and nutrient media for maintaining the plant cells in a live condition. A light source having desired optical characteristics is directed onto the plant cells and light spectra transmitted from the cells is detected by a photodetector. A controller analyzes signals from the photodetector to detect a state change in the plant cells in response to exposure to an agent.

13 Claims, 1 Drawing Sheet

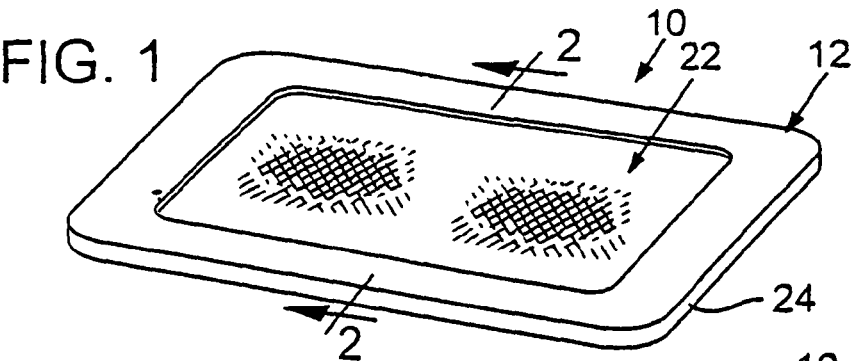
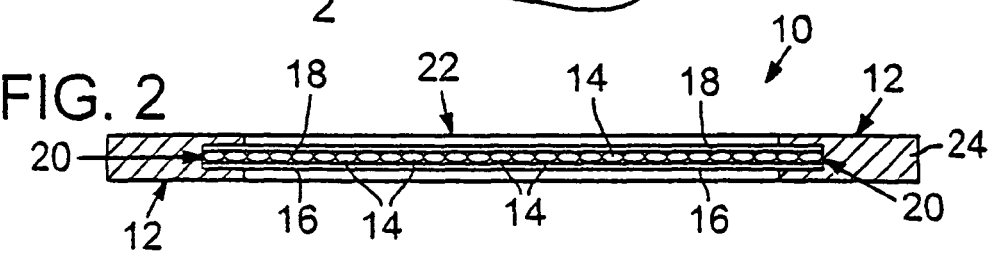
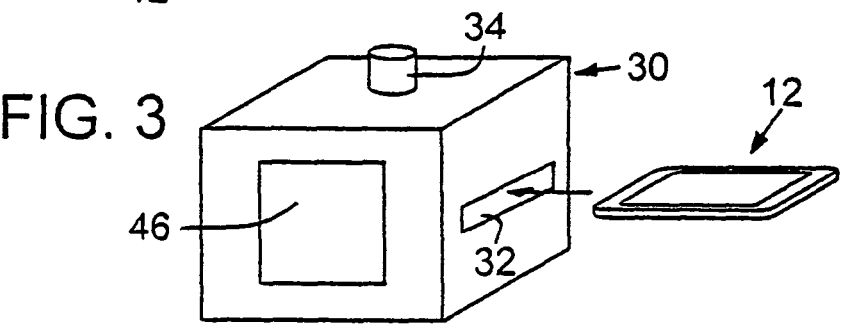
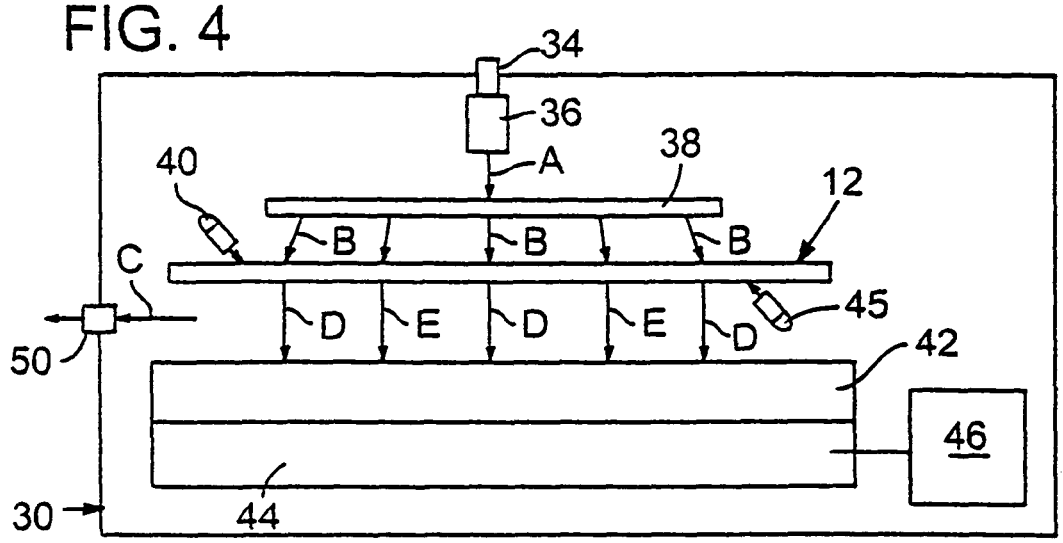

BIOSENSOR COMPRISING PLANT CELLS CAPABLE OF EXHIBITING A STATE CHANGE MEASURABLE OPTICALLY

Cross-Reference to Related Application

This application is a division of U.S. Patent Application Ser. No. 10/245,678, filed Sep. 16, 2002, now U.S. Patent No. 7,141,414, which is incorporated herein by reference.

TECHNICAL FIELD

This invention relates to biosensors useful for detecting the presence of biological and chemical compounds, and especially biologically hazardous agents.

BACKGROUND OF THE INVENTION

The ability to detect biological and chemical contaminants in a specific environment can be an important diagnostic tool in many different settings. For example, in any environment where an identified hazardous biological or chemical agent is known to exist, individuals who are called on to work in that environment are able to utilize appropriate protective measures such as protective clothing to avoid unintended exposure to the hazardous materials. But in many cases the presence of a hazardous biological or chemical agent may be suspected, but not confirmed. In those cases it is necessary to either provide adequate safety gear for personnel who might be exposed to the agent, or to complete a biohazard screening prior to exposing personnel to the environment. Neither solution fully addresses the problem. As to the former, it may not be possible to provide sufficient protective equipment for all individuals who might be exposed, and since the presence and/or type of biohazardous agent has not been confirmed, the correct type of protective gear necessary to ensure safety may not be available or chosen. As to the later, many screening tests require a significant amount of time to complete; there may not be sufficient time to complete analytical testing to confirm the presence, or absence of a biohazard before personnel are required to enter the area.

There is an ongoing and existing need, therefore, for apparatus and methods for rapidly detecting and confirming the presence of biological or chemical agents in a given environment.

Living cells are known to react to biological and chemical stimuli such as the stimuli caused by biohazardous compounds and materials. Live cells thus exhibit known physiological and morphological responses when exposed to other cells such as bacteria, viruses and molecules. And it is known that these cellular reactions to such compounds may be detected in various ways, including detecting changes in optical transmission properties of the cells, and through the use of indicator compounds. Various biosensors have been described that rely upon these known cellular reactions. However, such biosensors and the methodologies they use to detect biohazards do not adequately address the need for rapid qualitative determination of the presence of biohazardous compounds in a specific environment, tend to be too expensive, and are often difficult for untrained personnel to use.

SUMMARY

The illustrated embodiment comprises a biosensor utilizing plant cells and nutrient media for maintaining the plant cells in a live condition. A light source having desired optical characteristics is directed onto the plant cells and light spectra transmitted from the cells is detected by a photodetector. A controller analyzes signals from the photodetector to detect a state change in the plant cells in response to exposure to an agent.

BRIEF DESCRIPTION OF THE DRAWINGS

FIG. 1 is perspective schematic view of an illustrated embodiment of a biosensor according to the present invention as it is incorporated into a biosensor card.

FIG. 2 is a cross sectional view of the biosensor card illustrated in FIG. 1, taken along the line 2-2 of FIG. 1.

FIG. 3 is a schematic view of a biosensor analysis system for analyzing a biosensor card according to the illustrated embodiment.

FIG. 4 is a schematic view of an analytical unit for analyzing a biosensor card according to the illustrated embodiment, coupled to a computer.

DETAILED DESCRIPTION OF ILLUSTRATED EMBODIMENTS

A biosensor 10 according to an illustrated embodiment of the invention is shown in FIG. 1 incorporated into a biosensor card 12. As set forth in detail below, the biosensor 10 is capable of detecting the presence of biological and chemical agents, especially biohazardous environmental toxins and the like, through the detection of physiological and morphological changes in live plant cells upon exposure to the agents. Described generally, the biosensor 10 illustrated herein relies upon matrices of plant cells from live plant sources or tissue cultures that are maintained and kept alive in a nutrient-rich environment provided by translucent nutrient sheets. The specific type of plant cells used with the invention may be selected for their known physiological responses to the presence of environmental agents, including specific environmental agents. The cells exhibit physiological and/or morphological responses on exposure to agents, and those responses are manifest in several ways, including for example the opening and closing of stomates, cytoplasmic streaming, and changes in cytoplasmic pumping. These physiological responses may be detected with detection techniques such as changes in optical transmittance or reflectance, through chemical indicators, or combinations of optical transmittance or reflectance changes and chemical indicators. Changes in the state condition of the biosensor, as a result of changes in the optical character of light spectra transmitted from the plant cells and detected by various detectors, is transmitted to a controller such as a processor where the changes are analyzed and a response generated. The plant cells utilized in the illustrated invention thus function as biological switches.

Referring now to FIG. 2 it may be seen that biosensor 10 comprises a matrix of live plant cells 14 that are held between layers of nutrient sheets 16 and 18. As detailed below, the individual cells 14 comprise a cell matrix that exhibits some physiological or morphological response to environmental exposure to an agent. As such, the matrix of plant cells 14 is referred to herein as a receptor layer 20.

Although receptor layer 20 is comprised of plant cells, as used herein, the words "plant cell" refers to cells having certain characteristics rather than cells belonging to a specific taxonomic category of organism. Thus, as used herein, "plant cells" refers to cells that have relatively rigid cell walls, and which exhibit detectable physiologic and/or morphologic changes when the cells are exposed to environmental agents such as biological and/or chemical compounds. With reference to the cell walls of the plant cells used in connection with the invention, the cells are characterized by having a wall that is relatively rigid, and which is typically made up of complex polysaccharides such as cellulose and other complex saccharides, silica and the like. This cell wall structure is common in many classes of organisms and provides functional benefits that are useful in connection with the illustrated invention. By way of example, cells useful in connection with the illustrated invention include, without limitation, plant cells such as those described specifically below, and fungal cells, and cells of organisms that may not currently be characterized as belonging to the plant kingdom, such as chromista.

The relatively rigid cell walls found in such plant cells provide a stronger cellular structure that is useful for the purposes of biosensor 10 because the structure is resistant to structural changes. Compared to animal cells, plant cells manifest several characteristics that are beneficial for purposes of use as a biosensor. For example, when a matrix of cells such as receptor layer 20 is sandwiched between nutrient sheets as illustrated in FIG. 2, the rigid cell walls of the individual cells 14 resist dehydration, rupture caused by osmotic pressure, and likewise resists contraction and collapse. Owing in part to the structural rigidity derived from the cell wall, the plant cells thus tend to exhibit a longer life than animal cells would. In short, plant cells of the type described are more robust and longer-lived than other cell types.

With reference to the physiological and morphological characteristics that are of interest in the invention, the plant cells selected for use in connection with the invention are known to exhibit any detectable physiologic or morphologic response on exposure to environmental agents.

As used herein, the term "agent" refers generally to a compound present in an environment that causes a detectable cellular change in the plant cells 14. These agents include, for example, biological agents such as bacteria and viruses, and also molecules including chemical compounds. Within these broad categories are more specific classes of biological and chemical compounds, such as chemical toxins. The plant cells used herein respond to exposure to such biological and chemical compounds in many different ways, and these responses are manifest in changes in the cell structure or cellular activity that are detectable. Some of the specific physiological and morphological cellular responses include changes in the size of the individual cells, changes in the rate of biological pumping within the cells, increases or decreases in the rate of cytoplasmic streaming, and changes in the size of stomata such as is caused by the opening and closing of stomates.

As used herein, therefore, any detectable physiological or morphological change in a plant cell in response to exposure to an environmental agent is referred to as a "state" change. Stated in another way, the cell has reacted to exposure to an agent with a physiological or morphological response that is detectable, regardless of how that change in state is manifest.

Many classes of plant cells are known to exhibit state changes as that term is used herein. A few examples include plants from the Mimosa family, including Mimosa quadrivalvis and Mimosa pudica. Mimosa plants, including both of the varieties just mentioned, are known to have cellular pumps that react quickly to the type of external stimuli provided by environmental toxins. When such Mimosa cells are expose to certain classes of toxins the cells exhibit rapid changes in the rates of cytoplasmic streaming—a change in cellular physiology and morphology that is readily detectable as a state change. Other plant cells exhibit stomatic changes upon exposure to biological and chemical agents. Plant cells that include guard cells that surround stomates react to such agents by varying the size of the stomata. For example, stomata quickly close in some plant cells on exposure to certain classes of toxins. Still other plant cells such as Elodea and some members of the Papillonaceae exhibit changes in cellular streaming in the presence of toxins. These changes are detectable and are thus considered to comprise state changes as that term is used herein.

Referring again to FIG. 2, receptor layer 20 is sandwiched between two nutrient sheets 16 and 18. The nutrient sheets are selected according to the nutritional requirements of the specific type of plant cells 14 that are being used in the receptor layer, for their translucency and thus ability to transmit light, and for their ability to transmit gas across the sheets. Specifically, the nutrient sheets 16 and 18 comprise growth media such as an agar media formed into a sheet. Suitable nutrient sheets are commercially available from numerous sources.

Nutrient sheets meeting the criteria just mentioned are assembled into a layered arrangement with receptor layer 20 between sheets 16, 18. The three layers may be assembled with a biosensor card 12 that defines an open central portion 22 that is bordered by a border 24, which may be any appropriate material such as a stiff plastic or paperboard and the like. When assembled into a biosensor card 12 as illustrated in FIG. 2, the cells 14 that comprise receptor layer 20 are kept alive for a substantial period of time. The cards are easily and inexpensively manufactured, and are small and easily handled in the field. The cards may be packaged in individual packets with appropriate seals and internal packaging environments, or may be packaged in groups of more than one card. The border 24 functions as a support member for the two nutrient sheets and the receptor layer. Further, the nutrient sheets also act as a support member for supporting the receptor layer. In addition to other functions, both the border 24 and the nutrient sheets 16 and 18 thus serve to protect the cells 14 in receptor layer 20 from physical damage. Those of ordinary skill in the art will appreciate that the biosensor card 12 described herein is only one example of the many different structural configurations of support members that may be used to maintain a matrix of plant cells adjacent a nutrient media source.

The biosensor 10 described above is useful in combination with an analyzer to perform rapid assays to determine if target agents are present in a sample. Because the biosensor 10 is small, inexpensive and expendable, the system is especially well suited to use in the field. However, the system described herein may just as well be used in any other setting.

With reference to FIG. 3, an analyzer 30 is configured for detecting state changes in the receptor layer 20 of a biosensor card 12 that may be inserted into an analysis port 32 in the analyzer. As described below, analyzer 30 includes components suited for detecting state changes, analyzing those changes and reporting the results of the analysis. In a preferred embodiment, analyzer 30 is a self-contained unit that includes an sample intake manifold 34 that is fluidly coupled to a pump (not shown) for delivery of a sample of fluid to a biosensor card 12 that has been inserted into port 32. By way of example, if the sample to be analyzed is an air sample, the pump delivers air to biosensor card 12 while the card is in port 32. The air sample is delivered at a controlled rate and pressure, and the air is transported across nutrient layer 18 to expose receptor layer 20 to the sample. The air diffuses through the biosensor card under the pressure differential from the pump and is exhausted through an exhaust port, which is not shown. The analyzer includes hardware and software comprising analytical instrumentation as described below.

State changes in the cells 14 that comprise receptor layer 20 are detectable by changes in the optical character of light that is transmitted through and/or reflected from receptor layer 20. Plant cells are translucent, as are nutrient sheets 16 and 18, so light having desired optical characteristics maybe transmitted through the nutrient sheets and the receptor layer, and also may be reflected from the receptor layer. Referring now to FIG. 4 a schematic representation of analyzer 30 is illustrated. The analyzer includes a pump 36 plumbed to intake manifold 34 and configured for delivering a sample (for example, air) at the appropriate pressure and flow rate to biosensor card 12. A sample diffuser 38 may optionally be interposed between pump 36 and card 12 to disperse the air sample evenly across open portion 22 of the card. Analyzer 30 includes one or more analytical light sources configured for transmitting light having desired optical characteristics through the open portion 22 of biosensor card 12, and/or for reflecting such light off of the card. Thus, a first analytical light source 40 is oriented to direct transmit light through card 12 and onto photodetectors 42. Similarly, where reflected spectra are of interest, a second analytical light source 45 is oriented relative to the biosensor card to reflect light from the operative portions of the card and onto the photodetectors 42. Photodetectors 42 are interconnected with controllers such as processor 44, which includes appropriate processing capabilities, hardware and software, to analyze data received by the photodetectors and transmitted to the processor. Processor 44 analyzes data with predetermined algorithmic calculations and thus generates an output signal to a display 46, which may be any appropriate display such as a visually detectable unit such as a CRT or LCD screen, or as simple as an audible message generator such as a transducer.

The analytical steps illustrated in the schematic drawing of FIG. 4 will now be explained in detail. With biosensor card 12 inserted into port 32 of analyzer 30 (as shown in FIG. 3), light having the desired optical characteristics such as intensity and wavelength is transmitted with analytical light source 40 through the open central portion 22 of biosensor card 12 to produce transmitted spectra, illustrated with arrows D in FIG. 4. Alternately, light of the desired intensity and wavelength is reflected from the central portion 22 of the card to product reflected spectra, illustrated with arrows E in FIG. 4. As still another alternate, both transmitted and reflected spectra may be generated and analyzed. In either case the transmitted or reflected spectra is detected by photodetectors 42 and the resulting data are transmitted to processor 44, which is pre-programmed with analytical information and algorithms sufficient to process the data from the photodetectors. In the absence of a sample, the spectra detected by the photodetectors are utilized to generate a control state for the receptor sheet. The control state, or baseline, represents the condition of the receptor sheet in the absence of an agent that results in a state change, as that term is defined above.

Once the control state is determined the system is ready to analyze a sample. A sample to be analyzed is acquired by activating pump 36. Assuming for purposes of this example that the sample to be analyzed comprises air, the target sample is drawn into the analyzer through intake manifold 34 and is distributed to a sample diffuser 38, as shown with arrow A. Sample diffuser 38 distributes the sample across biosensor card 12, and more specifically across the open central portion 22 (FIG. 1) as illustrated with arrows B. As noted above, pump 36 is preset so that it delivers sample to the biosensor card at a predetermined desired flow rate and pressure at which the sample—in this case air—diffuses through nutrient sheet 16, across receptor layer 20, and through nutrient sheet 15. Once the sample air flows through the biosensor card it is exhausted through an exhaust port 50, shown schematically with arrow C.

The cells 14 of receptor layer 20 react to the presence of an agent in the sample with state change. This state change in the receptor layer 20 causes a change in the transmitted and/or reflected spectra, which in turn is received by the photodetectors 42. Processor 44 analyzes data from the photodetectors and if a state change is detected, outputs an appropriate warning signal to display 46. The processor may be programmed with instructions of varying complexity, depending upon the specific needs of the situation. For example, the processor may be programmed to include in its analysis the type of plant cells that are present in receptor layer 20, the specific physiological and/or morphological changes expected in that type of plant cell in response to a specific agent, and the expected effect that the state change has on the transmitted spectra. With this type of an analysis the processor may be used to output a signal that includes information about the specific type of agent that caused the state change. Relatively simpler output is attainable by programming the processor to output a YES/NO output. That is, if a state change is detected then a YES warning is output to display 46. On the other hand, if no state change is detected, then a NO signal is output to the display.

Those of ordinary skill in the art will recognize the flexibility and usefulness of the illustrated invention as a rapid assay tool for determining the presence of biohazardous materials in a sample. They will further recognize that various changes may be made to the features described above without departing from the scope of the illustrated invention. For example, different biosensor cards may be provided to test for different agents. One card may incorporate plant cells of a specific type that are known to react to the presence of biological agents such as bacterium. Another card may rely upon plant cells in receptor layer 20 that are known to react to the presence of viral particles. Still another card may utilize plant cells that react in know ways to certain classes of chemicals. And likewise, a card may be made using plant cells that are capable of reacting to a broad range of compounds. Moreover, the card may incorporate mixed cell cultures comprising cells from several different plant types in order to produce a biosensor that produces a state change in response to a wide variety of agents of differing types.

The card may optionally include machine-readable indicia such as a conventional bar code for providing information useful during analysis. For example, analyzer 30 may include a bar code reader and card 12 may include a bar code providing data regarding the type of cells 14 in the receptor layer, and that information may be used during analysis.

It is also possible to run an assay of a sample without establishing a control state in as a first step in the assay. If the biosensor card includes indicia indicating to the analyzer what cell types are present, the processor 44 may be preprogrammed with a value representing a control state value for that card. Any change in the control state value from the preprogrammed control state value will thus be interpreted as a state change. Even without preprogrammed information regarding the control state, a detected change in state during the time when the plant cells are being exposed to the sample may be used as an indicator of a state change.

The viability of the plant cells 14 may also be verified prior to running a test. Thus, processor 44 may be programmed with information relating to a known control state value for a particular type of cells in the receptor layer of a given biosensor card. When the processor detects a card 12 in port 34, through use of a bar code, the measured control state value at the time of the test routine may be compared to the known control state value for that particular card. If there is a difference between the known control state value and the determined state value, the difference may be due to a non-viable population of cells, indicating that the biosensor card is not functioning properly. A warning message may then be transmitted to the display 46 to inform the user of the condition.

Having here described illustrated embodiments of the invention, it is anticipated that other modifications may be made thereto within the scope of the invention by those of ordinary skill in the art. It will thus be appreciated and understood that the spirit and scope of the invention is not limited to those embodiments, but extend to the various modifications and equivalents as defined in the appended claims.

The invention claimed is:

1. A method of detecting the presence of an agent in a sample, comprising the steps of:
   (a) providing a biosensor comprising plant cells selected for the ability to exhibit a state change upon exposure to the agent, and nutrient media for maintaining the cells in a live condition, wherein the biosensor comprises a receptor layer including the plant cells, the receptor layer being sandwiched between two sheets of the nutrient media;
   (b) establishing a control state value for the biosensor by measuring one or more optical characteristics of the plant cells in the absence of a sample, the optical characteristics being selected from transmittance and reflectance of light;
   (c) exposing the biosensor to the sample;
   (d) measuring the optical characteristics of the plant cells exposed to the sample; and
   (e) comparing the optical characteristics measured with and without exposure to the sample to determine if a state change has occurred in the plant cells;
   wherein: the sample comprises air; exposing the biosensor to the sample includes diffusing the sample through the nutrient media to the plant cells; and the state change is a change in rate of cytoplasmic streaming or a change in size of stomata.

2. The method according to claim 1 including the step of generating a signal in response to a determination of a state change.

3. The method according to claim 1 including providing machine-readable indicia on the biosensor that correlates to identifying information for the biosensor.

4. The method according to claim 1 in which the control state value is established before exposing the biosensor to a sample.

5. The method according to claim 1 including the step of determining the viability of the plant cells.

6. The method of claim 1 wherein the biosensor is assembled into a biosensor card configured to be inserted into an analyzer that is configured to detect the state change.

7. A method of detecting the presence of an agent in a sample, comprising the steps of:
   (a) providing a biosensor comprising live cells and nutrient media for maintaining the cells in a live condition, wherein the biosensor comprises a receptor layer including the cells, the receptor layer being sandwiched between two sheets of the nutrient media;
   (b) maintaining the cells in a live condition;
   (c) exposing the cells to light and measuring transmittance or reflectance of the light by the cells to establish a first state condition;
   (d) exposing the cells to a sample;
   (e) exposing the cells, which have been exposed to the sample, to light and measuring transmittance or reflectance of the light by the cells to establish a second state condition; and
   (f) comparing the first state condition to the second state condition to determine if a state change has occurred;
   wherein: the sample comprises air; exposing the cells to a sample includes diffusing the sample through the nutrient media and to plant cells; and the state change is a change in rate of cytoplasmic streaming or a change in size of stomata.

8. The method according to claim 7 wherein the cells are plant cells selected for their ability to exhibit a state change upon exposure to an agent.

9. The method of claim 8 wherein the plant cells are selected from Mimosa plants, Elodea plants, Papilonaceae plants, and plant cells including guard cells that surround the stomata.

10. The method according to claim 7 wherein in step (c) the first state condition is a control state exhibited by the cells in the absence of an agent.

11. The method according to claim 7 wherein a state change occurs when the cells are exposed to an agent.

12. The method according to claim 11 wherein the agent is a biohazard.

13. A method of detecting the presence of an agent in a sample, comprising the steps of:
   (a) providing a biosensor comprising plant cells selected for the ability to exhibit a state change upon exposure to the agent, and nutrient media for maintaining the cells in a live condition;
   (b) establishing a control state value for the biosensor by measuring one or more optical characteristics of the plant cells in the absence of a sample, the optical characteristics being selected from transmittance and reflectance of light;
   (c) exposing the biosensor to the sample;
   (d) measuring the optical characteristics of the plant cells exposed to the sample; and
   (e) comparing the optical characteristics measured with and without exposure to the sample to determine if a state change has occurred in the plant cells;
   wherein: the sample comprises air; exposing the biosensor to the sample includes diffusing the sample through the nutrient media to the plant cells; and the state change is a change in size of stomata.

* * * * *